United States Patent
Tomic Stefanin et al.

(10) Patent No.: US 9,726,648 B2
(45) Date of Patent: Aug. 8, 2017

(54) METHOD AND SYSTEM FOR VERIFYING THE AGE OF AN ANIMAL PROVIDING MEAT

(71) Applicants: UNIVERSIDAD DE SANTIAGO DE CHILE, Santiago (CL); UNIVERSIDAD TECNICA FEDERICO SANTA MARIA, Valparaiso (CL)

(72) Inventors: Gerda Tomic Stefanin, Santiago (CL); José Silva Serrano, Santiago (CL); Cristián Acevedo Gutierrez, Valparaíso (CL); Elizabeth Sanchez Montiel, Valparaíso (CL); Manuel Young Anze, Valparaíso (CL)

(73) Assignees: UNIVERSIDAD DE SANTIAGO DE CHILE, Santiago (CL); UNIVERSIDAD TECNICA FEDERICO SANTA MARIA, Valparaiso (CL)

( * ) Notice: Subject to any disclaimer, the term of this patent is extended or adjusted under 35 U.S.C. 154(b) by 245 days.

(21) Appl. No.: 14/727,718

(22) Filed: Jun. 1, 2015

(65) Prior Publication Data
US 2015/0260692 A1 Sep. 17, 2015

Related U.S. Application Data

(63) Continuation of application No. 13/688,663, filed on Nov. 29, 2012, now Pat. No. 9,075,040.

(30) Foreign Application Priority Data

Jun. 11, 2012 (CL) .......................... 156612

(51) Int. Cl.
G01N 30/06 (2006.01)
G01N 1/22 (2006.01)
(Continued)

(52) U.S. Cl.
CPC ............... *G01N 30/06* (2013.01); *G01N 1/22* (2013.01); *G01N 1/405* (2013.01); *G01N 30/86* (2013.01);
(Continued)

(58) Field of Classification Search
CPC ........ G01N 30/06; G01N 30/86; G01N 33/12; G01N 33/497; G01N 1/22; G01N 1/405; G01N 2030/062
(Continued)

(56) References Cited

U.S. PATENT DOCUMENTS 7,781,160 B2 * 8/2010 Ryals ................... C12Q 1/6876
435/29
2003/0082597 A1 * 5/2003 Cannon ................ C12Q 1/6883
435/6.1

(Continued)

*Primary Examiner* — Peter Macchiarolo
*Assistant Examiner* — Nathaniel Kolb
(74) *Attorney, Agent, or Firm* — Karim Lagobi

(57) ABSTRACT

The invention provides a method for verifying the age of an animal providing meat using volatile profiles that comprises the step of providing a sample of animal meat. The method uses one or more chemical analyses to obtain a profile of a set of volatile organic compounds from a sample of meat from an animal. The profile is fit to a mathematically discriminating function resulting. The data obtained is analyzed in order to establish a correlation between the age of the animal (tooth development) and volatiles exuded by meat.

5 Claims, 3 Drawing Sheets

(51) Int. Cl.
*G01N 33/497* (2006.01)
*G01N 1/40* (2006.01)
*G01N 30/86* (2006.01)
*G01N 33/12* (2006.01)
G01N 30/88 (2006.01)

(52) U.S. Cl.
CPC ........... G01N 33/12 (2013.01); G01N 33/497 (2013.01); *G01N 2001/2229* (2013.01); *G01N 2030/062* (2013.01); *G01N 2030/8813* (2013.01)

(58) Field of Classification Search
USPC ........................................... 73/23.41
See application file for complete search history.

(56) References Cited

U.S. PATENT DOCUMENTS

| | | | | |
|---|---|---|---|---|
| 2004/0046567 | A1* | 3/2004 | Villinger | H01J 49/145 324/464 |
| 2008/0124752 | A1* | 5/2008 | Ryals | C12Q 1/6876 435/29 |
| 2010/0056898 | A1* | 3/2010 | McKenna | G01N 23/04 600/411 |
| 2010/0279337 | A1* | 11/2010 | Ryals | C12Q 1/6876 435/29 |
| 2012/0329057 | A1* | 12/2012 | Jang | C07K 16/18 435/6.12 |

* cited by examiner

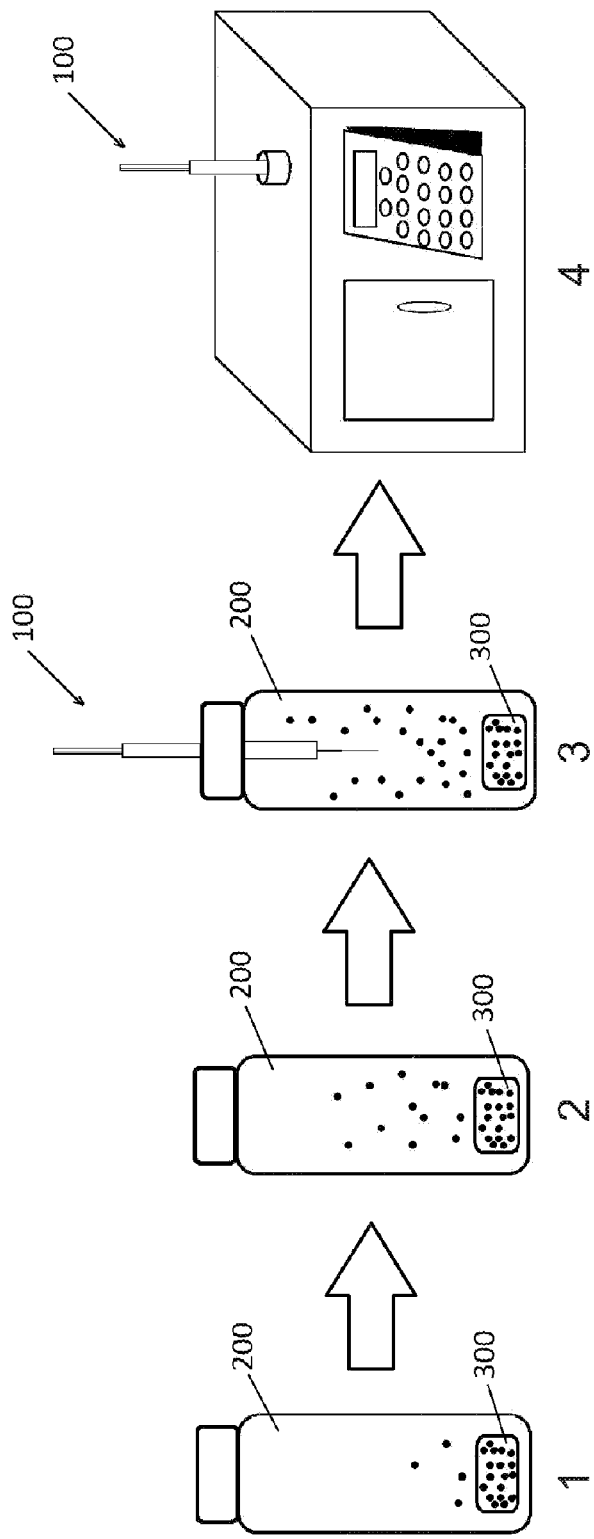

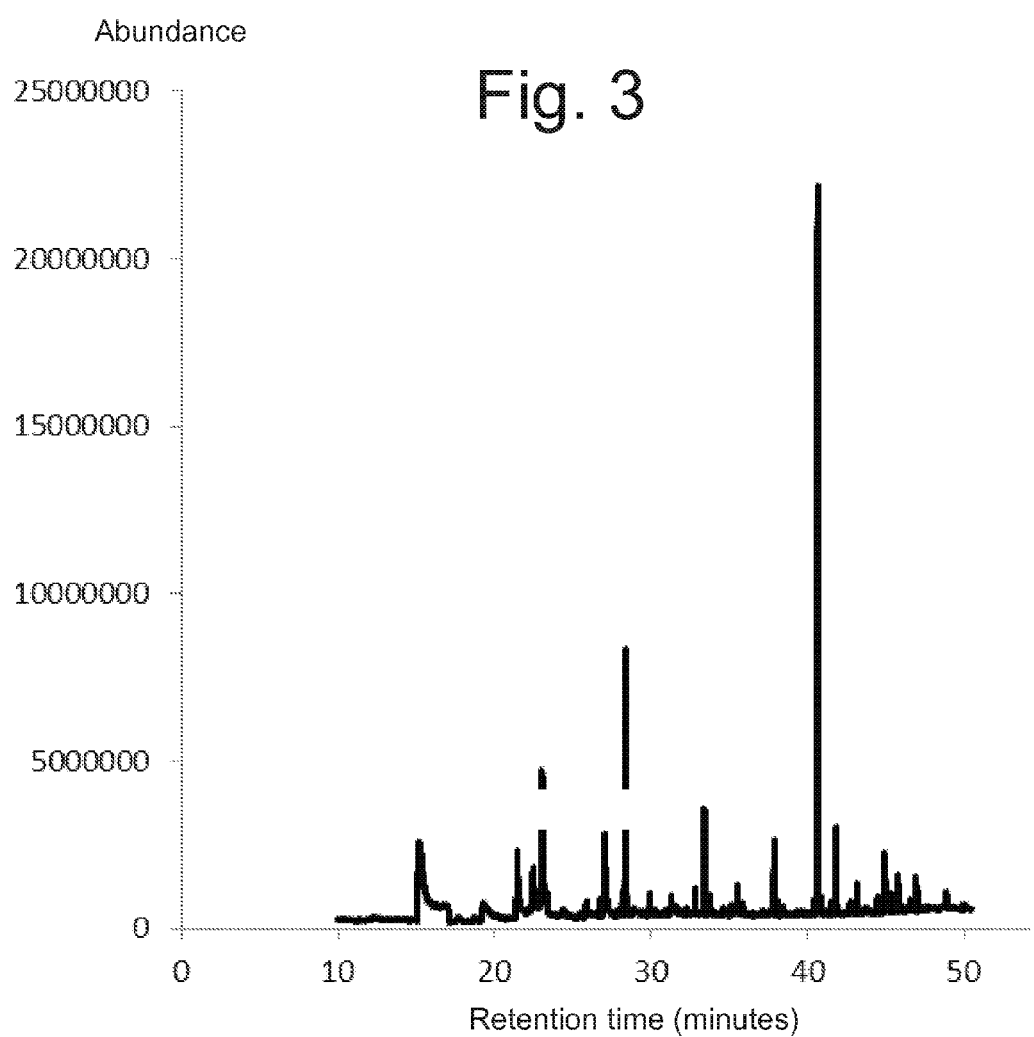

METHOD AND SYSTEM FOR VERIFYING THE AGE OF AN ANIMAL PROVIDING MEAT

CROSS-REFERENCES TO RELATED APPLICATIONS

The present application is a continuing patent application of U.S. patent application Ser. No. 13/688,663 filed on Nov. 29, 2012, now U.S. Pat. No. 9,075,040, which in turn claims priority to patent application No. 156612, filed on Nov. 6, 2012 in Chile. The entire text of each of the above-referenced applications is specifically incorporated by reference herein without disclaimer.

FIELD OF APPLICATION

This invention refers to identifying volatile compounds in meat and, more specifically, to an objective method for verifying the age in cut up meat, and more specifically to an analytical method, through which the characterization of volatile profiles verifies the age of animal meat in an objective manner.

DESCRIPTION OF THE PRIOR ART

The objective of the "Chile a food producing power" country strategy is to position the country as a strong food exporter. This has led to investing large sums of money to improve the country-image related to the quality of domestic production in accordance with market requirements, ensuring compliance with domestic and international regulations. In the case of the red meat market, traceability has been established as mandatory for all producers wishing to sell in Chile as well as overseas. Although traceability is an efficient system for quality assurance, its implementation and operational management is not an easy task and demands high resources at country level (private and government). As with all management systems, quality models based on traceability must be strictly controlled and audited in order to prevent the system from losing its credibility and affecting the transparency of the country-product, which would cause a critical situation for the entire national producing and exporting sector.

Today, there is no specific meat quality standard in place at national level. What is currently in effect and has some specific and direct relationship to quality are the standards indicated in Law 19.162 (known as the "Meat Law") and what is specified in the Food Sanitary Regulation (Supreme Decree 977 of 1996), in effect since 1997.

The aforementioned standards correspond to:

NCH 1306 of 2002 establishes the categorization requirements that must be complied with by butchered bits that are suitable for human consumption. Current standards are based on cattle the classification of livestock (by gender and age expressed in number of milk and permanent teeth), weight of the carcass in the case of calves, and the classification of their carcass considering such factors as the degree of fat cover and the degree of contusions (penalties).

NCH 1423 of 1994, which is related to the Classification, and provides the classes together with their names and the corresponding definition. This is based on gender and age factors by tooth development as indicated in the previous point.

NCH 1424 of 1994 refers to marking carcasses with their corresponding category and ink color (to be modified). The unique circular stamp that used to be double-stamped on the leg, rump and shoulder and which is now done only on the leg and shoulder in order to not damage the presentation of the strip loin.

NCH 1596 of 1999 refers to the nomenclature of the cuts used commercially and their anatomic location. The position indicated for the cuts of meat refers to the standing animal.

In accordance with these standards, beef is classified according to age and gender of the cattle. Age is determined by tooth development. The classes indicated in the standards correspond to: bull calf, bull, bullock, heifer, cow calf, adult cow, old cow, old bull, ox.

These classification and categorization systems are used to sort out the carcasses, placing them in categories according to the characteristics of the cattle and the consumer market. Different values are given in the categorization diagrams to carcasses already placed in the different categories. The basic characteristics that are commonly included in the categorization systems are age, gender, thickness of fat, hot carcass weight, shape, color of the meat and fat, texture of the meat, area of the loin eye, physiological maturity and defects.

Among the pre-mortem records that are included in the traceability of beef are the identification of and information on the animal, including its age when slaughtered. This parameter has proved to be fundamental in the sanitary status for the consumer and market competitiveness. A scenario that affects the market and food safety is bovine spongiform encephalopathy that is suspected to contribute to the appearance of Creutzfeld-Jacob syndrome, a highly mortal illness in humans. For safety and with the suspicion that what is described above may occur, it is wished to avoid the consumption of meat from animals over 30 months old. It is highly important to note that there are no analytical methodologies capable of objectively verifying the age of the cut up meat, since this is determined by tooth development at the time the animal is slaughtered, with traceability being the only alternative system to verify animal's age.

Nonetheless, for traceability to be solid, it must have verification mechanisms supporting it, so the creation of technology to support this system is absolutely necessary.

As regards the market, the categorization of beef carcasses together with the classification of cattle, in Chile as well as in most countries, constitutes a guiding standard for the commercialization of meat, and although each country has its own criteria, chronological age is incorporated into the majority of the classification and categorization systems in countries with developed cattle farming. In this sense, it is considered that the age of the animal at the time of slaughter is a key factor, since it imprints quality attributes on the meat that are intimately related to what the consumer and market considers in its appreciation of the quality of this product.

In this sense, it is of interest to the supervising or regulating entities to have objective tools to verify the age of categorized cut up meat, which allows to support supervisory action in sanitary and market matters.

On the other hand, volatile organic compounds (VOC) are a group of compounds that have organic carbon in their composition and a low boiling point, which allows them to vaporize into the air. The detection of VOCs is used for quality control processes, useful life studies, detection of contaminants and environmental monitoring, and is done generally using electronic noses (Braggins et al, 1999) and gas chromatography. For example, the patent document KR 20030079351, titled "METHOD FOR DETECTING VOLATILE COMPOUNDS OF IRRADIATED MEAT BY USING ELECTRONIC NOSE", describes the detection of volatile compounds of irradiated meat using an electronic nose, which includes the stages of: presenting different types of irradiated meat to the electronic nose with a matrix of sensors that comprises one or more metal oxide sensors; measuring the resistance of the sensor (RGA) exposed to the volatile compounds of irradiated meat, the measurement of the resistance sensor (Rair) in the air and the determination of a RGA/Rair resistance ratio; and applying the RGA/Rair resistance ratio of analysis of the principal components and analysis of neuronal networks, in which the meat oxide sensor comprises a hydrogen sulfate sensor, an ammonia sensor, a volatile vapor hydrocarbon sensor, an alcohol and an organic dissolvent steam sensor, an air contamination and a combustible gas sensor.

The gaseous phase that surrounds food is comprised of gases and vapors. The gases are compounds that are thermodynamically found in a gaseous state (above boiling temperature); however, they can solubilize in food, a process described by Henry's Law. On the other hand, vapors are molecules that are thermodynamically found in liquid state (below boiling temperature), but part of them can volatilize to the environment, a process described by Raoult's Law. In the last group are the volatile organic compounds "VOC". Some of these VOC are perceived by smell (Keverne, 2002), but a large number of them are not detected by human smell, since we do not have the ability to identify them or simply because they are below our detection threshold. However, modern analytical techniques such as gas chromatography (GC) allow detection and identification at low concentrations, information that has been used to study and characterize food. Hundreds of different types of VOC are in the emanations that generate the smells, which are functionally classified as: carboxylic acids, alcohols, aldehydes, aliphatics, esters, ketones, amines, heterocyclics and others. Studies conducted on mammals have shown that volatile emanations are a source of chemical signals that contain physiologically active volatile compounds that are capable of altering menstrual cycles, and vary depending on climate conditions and food, which indicates that VOC are part of complex biological systems. There is scientific evidence that indicates that the compounds present in the volatile profiles can be used as organic-volatile markers, that is, molecules that are produced only under specific circumstances. For example, there are volatile molecules that are only synthesized when a pathology takes place, and are used to verify the presence of a disease. Within this group it has been described that hexanal, heptanal, alkane derivatives, benzenes and aldehydes are exuded by people when they have some specific type of cancer. It is not difficult to imagine that different physiological conditions produce different compounds, which could volatilize and be used as biological tracers. Within this phenomenon can also be cited the senescent physiological status for which it seems reasonable to think that in different compounds emanate from meat from older animals than those that are habitually emanated by the meat from younger animals. If this is the case, there is the possibility of finding tracing molecules to determine if a sample of meat comes from a young or old animal, providing quantitative evidence for the categorization and classification of beef, since the main parameter is the age of the animal that is slaughtered. This idea is supported on the following scientific evidence: a) senescent conjunctive tissue cells emit a different volatile profile that young cells, and b) they have reported tracer molecules, such as lactones and terpenoids, which vary significantly according to the origin of the meat.

The study of VOCs in food has been carried out in order to identify those compounds that are responsible for aroma as a quality parameter. This is generally done through a gas chromatography analytical technique. Nonetheless, recent studies have used the chromatographic profile of a sample in different biological systems such as race, type of processing, origin, diet, anatomical section of the sample, etc.

The factors that influence the composition of the VOCs can be divided into two groups, factors of the animal (age, gender, species and race), and external or environmental factors (diet, weather, slaughtering conditions).

Due to the above, the general objective of this invention is to provide an analytical method that verifies the age of an animal's meat in an objective manner through the characterization of volatile profiles, especially of cattle, as well as pigs, sheep and poultry.

A first specific objective of this invention is to develop a technological platform for the measurement of volatile profiles in meat, especially of cattle, where the methodology of detection and measurement of volatile compounds exuded by the meat uses solid-phase micro-extraction (SPME) and gas chromatography (GC). The analytical chromatographic parameters are optimized in order to discriminate between different types of sample.

A second specific objective of this invention is to study profiles of volatile compounds in meat, especially cattle, analyzing volatile profiles of samples of meat of different ages, using samples with different categories of categorization and/or classification. The data obtained is analyzed in order to establish a correlation between the age of the animal (tooth development) and volatiles exuded by meat, especially cattle.

A third specific objective of this invention is to propose a methodology to verify the age of the meat, especially cattle, where a methodology for the objective verification of the age of the meat is established that is validated on site, and is established in the categorization of carcasses and/or classification of animals, especially cattle, using the measurement of volatile profiles. This methodology contains sampling and laboratory work protocols. The methodology allows the age of the animal from which the meat comes to be objectively verified and allows discrimination in the age barrier imposed for the export of red meat (prions similar to those of the Creutzfeld-Jacob syndrome).

SUMMARY OF THE INVENTION

An analytical method to verify the age of animal meat using volatile profiles that comprises the step of providing a sample of animal meat; finely cutting or chopping the sample of meat, eliminating all visible traces of fat to homogenize the sample; placing the sample of chopped meat in a vial with an hermetic septa; heating the vial with the sample of chopped meat inside it; providing a solid-phase micro-extraction fiber (SPME); placing the SPME fiber through the vial's septa; maintaining the SPME fiber inside the vial for a determined time; desorbing in the point of injection of a gas chromatograph, separating the gases so obtained in a chromatographic column; obtaining a chromatogram with a plurality of chromatographic peaks that represent volatile organic compounds (VOCs); Identifying VOCs from the chromatogram with mass spectrometry and confirming them with chemical standards; selecting a predetermined number of VOCs from the previous step and adjusting areas that are relative or absolute or concentrations or partial pressures of volatile organic compounds (VOCs) to a discriminating mathematical function to verify an objective limit of the animal's tooth development.

BRIEF DESCRIPTION OF DRAWINGS

FIG. 2 shows a sequential diagram of the adsorption of the analytes in the fiber inserted in a vial that contains a meat sample.

FIG. 3 shows a chromatogram of one of the measurements taken in this invention.

DETAILED DESCRIPTION OF THE INVENTION

Figure 1:
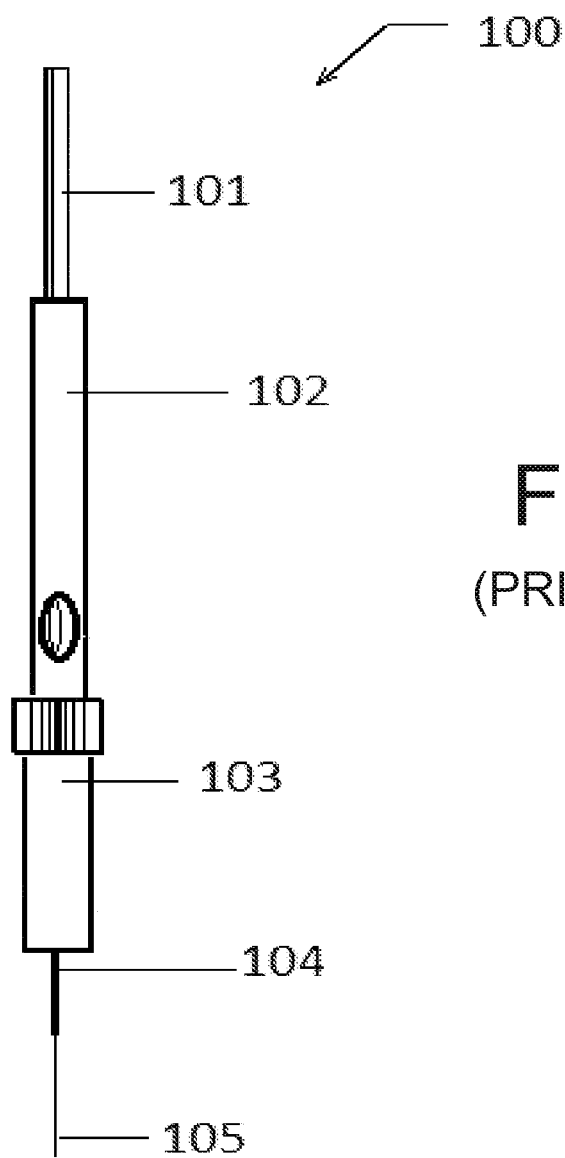
FIG. 1 (Prior Art) shows a solid-phase micro-extraction system (SPME).

Since there are volatile compounds that are generated under specific age-related physiological characteristics, this invention proposes a method to determine volatile profiles exuded by types of meat, especially bovine cattle, as well as that of pigs, sheep and poultry of different ages.

The solution consists of the development of an analytical technological platform, using equipment available in chemical laboratories, such as gas chromatographs. To this effect, the gas chromatography and solid-phase micro-extraction technique, known as GC-SPME, is used, a technique sparingly used in technological applications for food certification, since it has been recently developed. The volatile profiles obtained are correlated to age using a mathematical function, which generates an algorithm for the objective verification of the age of the cut up meat.

As shown in FIG. 1 (prior art), the SPME technique consists of a process of extraction and pre-concentration of the sample which is done simultaneously in one sole step. It includes a short capillary column (100) open to the environment and contained in a retractable pin (101), which includes the syringe barrel (102), a central body (103) that ends in a needle (104), which contains a silica fiber (105).

The SPME column (100) is a fiber covered with a phase used for extraction, which can be constituted of a polymer or an adsorbing solid, allowing a large number of volatile analytes to be retained, if applied over the head space of a sample. As shown in FIG. 2, a sample (300) is placed inside a vial (200), where this sample (300) begins to free the VOCs (step 1); after a while the VOCs are accumulated inside the vial (step 2). Subsequently, the SPME fiber (100), contained in a retractable mechanical pin (101), is inserted in a vial (200) through a septa. After the fiber is inserted in the vial (200), the retractile system exposes the fiber to the head space, adsorbing the volatiles exuded by the sample (step 3). Then, the volatiles are analyzed by gas chromatography (GC) when the SPME fiber (100) is placed in this GC (step 4).

A sample of meat is placed in an HS vial (Head Space) with an airtight septa, through which the solid-phase micro-extraction fiber is introduced, which is then in contact with the vial's head space. The sample inside the vial is subjected to a thermal process within a 0-100° C. temperature range.

After the adsorption of the analytes in the fiber, they are desorbed directly at the gas chromatograph port.

The volatile compounds that are correlated to the animal's age or tooth development are measured and a mathematical function that associates their concentration, relative concentration, chromatographic area, relative area or partial pressure with the age of the animal or tooth development is used.

EXAMPLE OF APPLICATION

Samples of fresh meat were taken (Longissimus dorsi, strip loin) from 8 groups of animals with different stages of tooth development and gender. 5 animals were sampled per group and each sample was analyzed in triplicate, obtaining 120 measurements (8×5×3=120).

TABLE 1

Samples of Fresh Meat according to age and gender

| Sample group | Permanent teeth | Gender |
|---|---|---|
| Group 1 | 1 | Male |
| Group 2 | 2 | Male |
| Group 3 | 4 | Male |
| Group 4 | 6 | Male |
| Group 5 | 2 | Female |
| Group 6 | 4 | Female |
| Group 7 | 6 | Female |
| Group 8 | 8 | Female |

A 2.5 gram sample was placed in a 20 ml HS vial. The vial was sealed and heated at 50° C. for 30 minutes. A commercial 50/30 μm Divinylbenzene/Carboxen-Polydimethylsiloxane SPME type fiber was placed through the septa and kept in the vial's head space for 30 minutes. The fiber was then desorbed in the injection port of a Thermo Scientifics Trace GC Ultra gas chromatographer equipped with a quadrupole mass spectrometer (Thermo Scientifics ISQ) at 250° C. for 5 minutes (splitless mode for 5 minutes). The separation was carried out in a Restek RTX-5MS brand column, 60 meters long, using helium at a constant flow of 1.3 ml/min. The initial temperature of the chromatograph oven was 40° C. and the end temperature was 250° C. The operation of the chromatograph equipment was controlled through Finnigan Xcalibur Software (Thermo Electron Corporation).

As shown in FIG. 3 and through this chromatographic procedure, a chromatogram signal was obtained with over 40 chromatographic peaks. Of these chromatographic peaks, 17 were identified with a mass spectrometer and were confirmed with chemical standards:

TABLE 2

Identification of Compounds using spectrometry

| Retention time | Compounds |
|---|---|
| 12.83 | n-Pentanol |
| 17.63 | n-hexanol |
| 21.78 | Benzaldehyde |
| 22.42 | Hexanoic acid |
| 24.32 | 2-ethyl-1hexanol |
| 25.83 | Octanol |
| 26.95 | Nonanal |
| 28.87 | Benzoic acid |
| 29.00 | Octanoic acid |
| 30.15 | Decanal |
| 31.84 | Nonanoic acid |
| 32.79 | Tridecanol |
| 35.47 | Tetradecanol |
| 36.85 | 4-Formil, benzoic acid |
| 38.00 | Pentadecanol |
| 40.38 | Hexadecanol |
| 42.69 | Heptadecanol |

Of these 17 compounds, 7 VOCs were selected and their relative areas were adjusted to a discriminating mathematical function to verify an objective limit of tooth development. In this example, the limit of 4 permanent teeth was used, which corresponds to type V meats for Chilean categorization. A precision above 90% was obtained.

Categorization Algorithm for Type V Fresh Meat
Discriminant Mathematical Function $$Y=6.074-0.077X_1-0.046X_2-0.072X_3-0.068X_4-0.068X_5-0.043X_6-0.071X_7$$

Decision Rule

If Y>0 tooth development less than or equal to 4 permanent teeth (type V meat).

If Y<0 tooth development more than 4 permanent teeth

Nomenclature

| | |
|---|---|
| Y | Discriminant Variable |
| $X_1$ | Hexanoic acid |
| $X_2$ | Octanol |
| $X_3$ | Nonanal |
| $X_4$ | Benzoic Acid |
| $X_5$ | Octanoic Acid |
| $X_6$ | Tridecanol |
| $X_7$ | Tetradecanol |

TABLE 3

Detail of the precision of the discriminant algorithm

| | Discriminated as | | | |
|---|---|---|---|---|
| Sample | Less than or equal to 4 teeth | Over 4 teeth | Total | Accuracy |
| Type V meat | 70 | 5 | 75 | 93.30% |
| Other types | 4 | 41 | 45 | 91.10% |
| Total | 74 | 46 | 120 | 92.50% |

The invention claimed is:

1. A method for verifying the age of animal meats using volatile compounds profiles comprising the steps of:
   obtaining a sample of meat of an animal;
   obtaining a homogenized sample of meat by finely cutting said sample of meat and eliminating all visible traces of fat;
   placing said homogenized sample meat in in a lower part of a vial having an hermetic septa and a head space;
   heating said vial to a temperature between 0 and 100° C. for between 1 and 500 minutes;
   introducing a solid-phase micro-extraction fiber into said septa of said vial;
   maintaining said solid-phase micro-extraction fiber in said vial's head space for at least 5 minutes;
   obtaining gases by desorbing in the point of injection of a gas chromatograph;
   separating said gases obtained in a chromatographic column using helium at a constant flow;
   obtaining a chromatogram having a plurality of chromatographic peaks representing volatile organic compounds;
   identifying said volatile organic compounds in said chromatogram;
   selecting a subset of said volatile organic compounds identified in said chromatogram, wherein the areas of said chromatogram corresponding to said subset are adjusted to a mathematically discriminating function; and
   obtaining an objective limit of tooth development of said animal using an output of said mathematically discriminating function;
   wherein the discriminant mathematical function comprises:

$$Y=6.074-0.077X_1-0.046X_2-0.072X_3-0.068X_4-0.068X_5-0.043X_6-0.071X_7$$

where:
Y Discriminant variable
$X_1$ Hexanoic acid
$X_2$ Octanol
$X_3$ Nonanal
$X_4$ Benzoic acid
$X_5$ Octanoic acid
$X_6$ Tridecanol
$X_7$ Tetradecanol.

2. The method of claim 1, wherein said step of heating said vial further comprising heating said vial to a temperature of 50° C. for 30 minutes.

3. The method of claim 1, wherein said step of maintaining said solid-phase micro-extraction fiber in said vial's head space further comprising maintaining said solid-phase micro-extraction fiber in said vial's head space for 30 minutes.

4. The method of claim 1, wherein if "Y" is greater than zero, then the tooth development is less than or equal to a pre-established limit of the animal's permanent teeth.

5. The method of claim 4, wherein if "Y" is less than zero, then the tooth development is greater than the pre-established limit of the animal's permanent teeth.

* * * * *